United States Patent [19]

Chang et al.

[11] 4,086,262

[45] Apr. 25, 1978

[54] CONVERSION OF SYNTHESIS GAS TO HYDROCARBON MIXTURES

[75] Inventors: Clarence D. Chang, Princeton; William H. Lang, Pennington, both of N.J.; Anthony J. Silvestri, Morrisville, Pa.

[73] Assignee: Mobil Oil Corporation, New York, N.Y.

[21] Appl. No.: 733,982

[22] Filed: Oct. 20, 1976

Related U.S. Application Data

[63] Continuation-in-part of Ser. No. 724,485, Sep. 20, 1976, abandoned, and Ser. No. 463,711, Apr. 24, 1974, abandoned.

[51] Int. Cl.$^2$ .................. C07C 1/04; C07C 1/16
[52] U.S. Cl. .................. 260/449.6 R; 260/449 R; 260/449 M; 260/449.6 M; 252/455 Z
[58] Field of Search ....... 260/449 R, 449 M, 449.6 R, 260/449.6 M

[56] References Cited

U.S. PATENT DOCUMENTS

| | | | |
|---|---|---|---|
| 1,834,621 | 12/1931 | Jaeger | 260/449.6 |
| 1,840,450 | 1/1932 | Jaeger et al. | 260/449.6 |
| 1,925,389 | 9/1933 | Jaeger | 260/449.6 |
| 2,567,259 | 9/1951 | Watson | 260/449 |
| 2,567,596 | 9/1951 | Clark | 260/449 R |
| 2,637,739 | 5/1953 | McGrath | 260/449.6 |
| 2,727,055 | 12/1955 | Seelig et al. | 260/449 R |
| 2,754,314 | 7/1956 | McGrath | 260/449 R X |
| 2,850,515 | 9/1958 | Riblett et al. | 260/449.6 |
| 3,013,990 | 12/1961 | Breck et al. | 260/455 Z |
| 3,254,023 | 5/1966 | Miale et al. | 260/449 R |
| 3,702,886 | 11/1972 | Argauer et al. | 423/328 |
| 3,709,979 | 1/1973 | Chu | 252/455 Z |
| 3,972,958 | 8/1976 | Garwood et al. | 260/449 R |

FOREIGN PATENT DOCUMENTS

| | | | |
|---|---|---|---|
| 828,228 | 10/1975 | Belgium | 260/449 |
| 1,036,837 | 8/1950 | Germany | 260/449 |
| 762,705 | 12/1956 | United Kingdom | 260/449.6 |

OTHER PUBLICATIONS

Abdulahad et al., Brennstoff Chemie 25, No. 4, (1972), 187–188.
Storch et al., Fischer Tropsch & Related Syntheses, John Wiley, New York, 1951, 428–436, 454–458.

*Primary Examiner*—Howard T. Mars
*Attorney, Agent, or Firm*—Charles A. Huggett; Michael G. Gilman

[57] ABSTRACT

Contacting a mixture of carbon monoxide and hydrogen with an intimate mixture of a carbon monoxide reduction catalyst, such as a Fischer-Tropsch catalyst or a methanol synthesis catalyst, and an acidic crystalline aluminosilicate having a pore dimension greater than about 5 Angstroms to produce hydrocarbon mixtures useful in the manufacture of heating fuels, high octane gasoline, aromatic hydrocarbons, and chemicals intermediates.

10 Claims, No Drawings

CONVERSION OF SYNTHESIS GAS TO HYDROCARBON MIXTURES

BACKGROUND OF THE INVENTION

1. Field of the Invention

This invention is concerned with an improved process for converting synthesis gas, i.e., mixtures of gaseous carbon oxides with hydrogen or hydrogen donors, to hydrocarbon mixtures. In one aspect, this invention is particularly concerned with a process for converting synthesis gas to hydrocarbon mixtures rich in aromatic hydrocarbons. In another aspect, this invention is concerned with a process for converting synthesis gas to hydrocarbon mixtures particularly rich in liquefiable petroleum gases such as propane. In still another aspect, this invention is concerned with providing novel catalysts for the conversion of synthesis gas to hydrocarbon mixtures.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in encyclopedia of Chemical Technology, Edited by Kirk-Othmer, Second Edition, Volume 10, pages 353–433, (1966), Interscience Publishers, New York, N.Y., the contents of which are herein incorporated by reference. The techniques for gasification of coal or other solid, liquid or gaseous fuel are not considered to be per se inventive here.

It would be very desirable to be able to effectively convert synthesis gas, and thereby coal and natural gas, to highly valued hydrocarbons such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, at from about 300° F to about 850° F, under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. The types of catalysts that have been studied for this and related processes include those based on metals or oxides of iron, cobalt, nickel, ruthenium, thorium, rhodium and osmium.

The wide range of catalysts and catalyst modifications disclosed in the art and an equally wide range of conversion conditions for the reduction of carbon monoxide by hydrogen provide considerable flexibility toward obtaining selected boiling-range products. Nonetheless, in spite of this flexibility, it has not proved possible to make such selections so as to produce liquid hydrocarbons in the gasoline boiling range which contain highly branched paraffins and substantial quantities of aromatic hydrocarbons, both of which are required for high quality gasoline, or to selectively produce aromatic hydrocarbons particularly rich in the benzene to xylenes range. A review of the status of this art is given in "Carbon Monoxide-Hydrogen Reactions", Encyclopedia of Chemical Technology, Edited by Kirk-Othmer, Second Edition, Volume 4, pp. 446–488, Interscience Publishers, New York, N.Y., the text of which is incorporated herein by reference.

Recently it has been discovered that synthesis gas may be converted to oxygenated organic compounds and these then converted to higher hydrocarbons, particularly high octane gasoline, by catalytic contact of the synthesis gas with a carbon monoxide reduction catalyst followed by contacting the conversion products so produced with a special type of zeolite catalyst in a separate reaction zone. This two-stage conversion is described in copending U.S. patent application, Ser. No. 387,220, filed on Aug. 9, 1973. Compositions of iron, cobalt or nickel deposited in the inner absorption regions of crystalline zeolites are described in U.S. Pat. No. 3,013,990. Attempts to convert synthesis gas over X-zeolite base exchanged with iron, cobalt and nickel are described in Erdöl und Kohle — Erdgas, Petrochemie: Brennstoff — Chemie, Vol. 25, No. 4, pp. 187–188, April 1972.

It is an object of the present invention to provide an improved process for converting fossil fuels to a hydrocarbon mixture that contains large quantities of highly desirable constituents. It is a further object of this invention to provide a more efficient method for converting a mixture of gaseous carbon oxides and hydrogen to a mixture of hydrocarbons. It is a further object of this invention to provide an improved method for converting synthesis gas to a hydrocarbon mixture rich in aromatic hydrocarbons. It is a further object of this invention to provide a method for converting synthesis gas to petrochemicals feedstocks, including olefins. It is a further object of this invention to provide an improved method for converting synthesis gas to propane fuel. It is a further object of this invention to provide novel catalysts for the conversion of synthesis gas.

BRIEF SUMMARY OF THE INVENTION

It has now been discovered that valuable hydrocarbon mixtures may be produced by reacting synthesis gas, i.e., mixtures of hydrogen gas with gaseous carbon oxides, or the equivalents of such mixtures, in the presence of certain heterogeneous catalysts comprising intimate mixtures of two components. The effective intimate mixtures, as will be more fully described hereinafter, are those in which the first component is selected from the class of inorganic substances that have catalytic activity for the reduction of carbon monoxide, and the second component is an acidic crystalline aluminosilicate. Depending on the choice of components and the particular reaction condition, one may obtain substantial quantities of liquid mixtures which are rich in branched paraffins and aromatic hydrocarbons and eminently suited for making high octane gasoline or petrochemicals. Alternatively, one may select catalyst and operating conditions in such a manner, as will hereinafter be described, to produce normally gaseous hydrocarbons having at least one carbon-to-carbon bond as the predominant product, or hydrocarbon streams rich in internal olefins. Such products have value as petrochemical feedstocks, and for the manufacture of liquefiable petroleum fuel. The intimate mixtures, some of which are distinctly novel, not only produce highly desirable products with good selectivity but in many cases produce them either with extraordinarily high conversion per pass, or under mild conditions, or sometimes both. With thoria as the carbon monoxide reducing component, synthesis gas is converted at surprisingly low temperature and pressure. With a methanol synthesis catalyst of the zinc-copper-chromite-type as the reducing component, synthesis gas conversion rate is increased and large proportions of hydrocarbons having at least one carbon-to-carbon bond are obtained instead of methanol. With Fischer-Tropsch-type catalysts, increased quantities of aromatic hydrocarbons are obtained. In general, it is surprisingly easy to achieve increased proportions of aromatics when a Fischer-Tropsch-type catalyst is used as the reducing component. Furthermore, when the preferred acidic crystalline aluminosilicate component is used in the intimate mixture, the catalytic activity is sustained for unusually long periods of time and the aromatic hydrocarbons, when produced, are very rich in toluene and xylenes.

DETAILED DESCRIPTION AND PREFERRED EMBODIMENTS

Synthesis gas for use in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials also may be used.

The raw synthesis gas produced from fossil fuels will contain various impurities such as particulates, sulfur, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention. However, it may not be necessary to remove substantially all the sulfur impurities when thoria is used as the carbon monoxide reducing component, since thoria is relatively little affected by sulfur compounds. Furthermore, should it be required, it is preferred to adjust the hydrogen-to-carbon oxides volume ratio to be within the range of from 0.2 to 6.0 prior to use in this invention. Should the purified synthesis gas be excessively rich in carbon oxides, it may be brought within the preferred range by the well known water-gas shift reaction. On the other hand, should the synthesis gas be excessively rich in hydrogen, it may be adjusted into the preferred range by the addition of carbon dioxide or carbon monoxide. Purified synthesis gas adjusted to contain a volume ratio of hydrogen-to-carbon oxides of from 0.2 to 6.0 will be referred to as adjusted synthesis gas.

It is contemplated that the synthesis gas for use in this invention includes art-recognized equivalents to the already-described mixtures of hydrogen gas with gaseous carbon oxides. Mixtures of carbon monoxide and steam, for example, or of carbon dioxide and hydrogen, to provide adjusted synthesis gas by in situ reaction, are contemplated. Furthermore, when the novel process of this invention is used to produce hydrocarbon mixtures rich in aromatic hydrocarbons, as will be more fully described, a hydrogen-donor such as methane, methanol, or higher alcohols may be charged with the gaseous carbon oxides mixture to some advantage.

The heterogeneous catalysts of this invention comprise two components intimately mixed, and in which one component is selected from the class of inorganic substances that have catalytic activity for the reduction of carbon monoxide, and in which the other component is an acidic crystalline aluminosilicate characterized by a pore dimension greater than about 5 Angstroms and a silica-to-alumina ratio of at least 2.5.

The component characterized by catalytic activity for the reduction of carbon monoxide may be selected from any of the art-recognized catalysts for producing hydrocarbons, oxygenated products, or mixtures thereof, from synthesis gas. Broadly, these components include those recognized as methanol synthesis catalysts, Fischer-Tropsch synthesis catalysts, and variants thereof. Commercial methanol synthesis catalysts comprising metals or oxides of zinc together with chromia, or of zinc and copper together with chromia or alumina, or known modifications of these, are included. In fact, synthesis gas will undergo conversion to form reduction products of carbon monoxide, such as alcohols and hydrocarbons, at from about 300° F to about 850° F, under from about 1 to 1000 atmospheres pressure, over a fairly wide variety of catalysts. The prominent types of catalyst that induce conversion include the metals or oxides of zinc, iron, cobalt, nickel, ruthenium, thorium, rhodium and osmium. Fischer-Tropsch-type catalysts based on iron, cobalt, or nickel, and especially iron, are particularly suited for the production of oxygenated and hydrocarbon products that have at least one carbon-to-carbon bond in their structure. With the exception of ruthenium, all practical, art-recognized synthesis catalysts contain chemical and structural promoters. These promoters include copper, chromia, alumina, the alkaline earths, the rare earths, and alkali. Alkali, e.g., the carbonates of Group IA of the periodic table, and especially of potassium, is of particular importance with iron catalysts, since it greatly enhances the conversion efficiency. Supports such as kieselguhr sometimes act beneficially.

It should be recognized that the carbon monoxide reducing component may be furnished as elemental metal or as corresponding metal compounds. Frequently in the preparation and use of such catalytic substances there will be one or more partial or complete transformations from elemental metal to compound, or vice versa. By way of illustration, pure iron, roasted in an oxygen atmosphere in the presence of added aluminum and potassium nitrates provides a composition that contains 97% $Fe_3O_4$, 2.4% $Al_2O_3$, and 0.6% $K_2O$ with trace amounts of sulfur and carbon. This composition after reduction with hydrogen at about 850° F catalyzes the conversion of synthesis gas at from 350° to 430° F, and at 20 atmospheres pressure, such that 65% of the carbon monoxide is reduced to a mixture consisting of about one-third by weight of hydrocarbons boiling in the range of 200° F to about 680° F, and about two-thirds of oxygenated compounds mostly alcohols, in the same boiling range. Manganese nodules may be used as catalyst.

It is preferred, for the purpose of this invention, to utilize as one component of the heterogeneous catalyst a substance that has catalytic activity for the reduction of carbon monoxide to organic products having at least one carbon-to-carbon or carbon-to-oxygen bond. Prominent substances of this type include the metals or oxides of zinc, iron, cobalt, ruthenium, thorium, rhodium, and osmium. Particularly preferred substances are the metals or oxides of zinc, iron, cobalt, ruthenium and thorium. The inorganic substance that has catalytic activity for the reduction of carbon monoxide should in all cases constitute from 0.1% to 99% by weight, and preferably from 1% to 80% by weight of the active components of the intimate mixture.

The acidic crystalline aluminosilicate component of the heterogeneous catalyst is characterized by a pore dimension greater than about 5 Angstroms, i.e., it is capable of sorbing paraffins having a single methyl branch as well as normal paraffins, and it has a silica-to-alumina ratio of at least 2.5. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

Zeolites useful for the crystalline aluminosilicate component of this invention include the acidic forms of: zeolite X, described in U.S. Pat. No. 2,882,244; zeolite Y, described in U.S. Pat. No. 3,130,007; mordenite; zeolite L, described in U.S. Pat. No. 3,216,789; zeolite T, described in U.S. Pat. No. 2,950,952; and zeolite beta, described in U.S. Pat. No. 3,308,069. The acidic crystalline aluminosilicate component should be in the hydrogen form, or it may be stabilized by ion exchange with rare earth or other metal cations that need not contribute to the carbon monoxide reducing function.

The preferred zeolites useful in this invention are selected from a recently discovered novel class of zeolites with unusual properties. These zeolites by themselves induce profound catalytic transformations of aliphatic hydrocarbons to aromatic hydrocarbons. Although they have unusually low alumina contents, i.e., high silica-to-alumina ratios, they are very active even when the silica-to-alumina ratio exceeds 30. The activity is surprising since the alumina in the zeolite framework is believed responsible for catalytic activity. These catalysts retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. Equally important, when used as the acidic crystalline aluminosilicate component in the process of this invention, the process selectively produces relatively large amounts of aromatic hydrocarbons in the benzene to xylenes range, and the intimate mixtures have catalytic activity which is sustained for unusually long periods of time.

An important characteristic of the crystal structure of this preferred class of zeolites is that it provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred acidic crystalline aluminosilicates useful in this invention possess, in combination: a silica-to-alumina ratio of at least about 12; and a structure providing constrained access to the intracrystalline free space.

The silica-to-alumina ratio referred to may be determined by conventional analysis. This ratio is meant to represent, as closely as possible, the ratio in the rigid anionic framework of the zeolite crystal and to exclude alumina in the binder or in cationic form within the channels. Although acidic crystalline aluminosilicates with a silica-to-alumina ratio of at least 12 are useful, it is preferred to use those having higher ratios of at least about 30. Such solids, after activation, acquire an intracrystalline sorption capacity for normal hexane which is greater than that for water, i.e., they exhibit "hydrophobic" properties. It is believed that this hydrophobic character is advantageous in the present invention.

The preferred crystalline aluminosilicates useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight-membered rings or oxygen atoms, then access to molecules of larger cross-section than normal hexane is excluded and the zeolite is not of the desired type. Windows of ten-membered rings are preferred, although excessive puckering or pore blockage may render these catalysts ineffective. Twelve-membered rings do not generally appear to offer sufficient constraint to produce the advantageous selectivity, although structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° F and 950° F to give an overall conversion between 10 percent and 60 percent. The mixture of hydrocarbons is passed at 1 liquid hourly space velocity (i.e., 1 volume of hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons. The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index from 1.0 to 12.0, preferably 2.0 to 7.0.

The preferred class of zeolites defined herein is exemplified by ZSM-5, ZSM-11, ZSM-12, ZSM-21, TEA mordenite and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. Application Ser. No. 358,192, filed May 7, 1973, the entire contents of which are incorporated herein by reference, which application has been abandoned in favor of U.S. Application Ser. Nos. 528,060 and 528,061, filed Nov. 29, 1974, directed to ZSM-38 and 35 respectively, the apparent component zeolites of ZSM-21, the entire contents of which are incorporated herein by reference. Ser. No. 528,061 has matured into U.S. Pat. No. 4,016,245. Ser. No. 528,060 has been abandoned in favor of Ser. No. 560,412 which has matured into U.S. Pat. No. 4,046,859.

The specific preferred zeolites described, when prepared in the presence of organic cations, are catalytically inactive, possibly because the intracrystalline free space is occupied by organic cations from the forming solution. They may be activated by heating in an inert atmosphere at 1000° F for 1 hour, for example, followed by base exchange with ammonium salts followed by calcination at 1000° F in air. The presence of organic cations in the forming solution may not be absolutely essential to the formation of this special type zeolite; however, the presence of these cations does appear to favor its formation. Regardless of preparation technique, it is desirable to activate this type zeolite by base exchange with ammonium salts followed by calcination in air at about 1000° F for from about 15 minutes to about 24 hours.

Natural zeolites may sometimes be converted to this preferred type zeolite by various activation procedures and other treatments such as base exchange, steaming, alumina extraction and calcination, in combinations. Natural minerals which may be so treated include ferrierite, brewsterite, stillbite, dachiardite, epistilbite, heulandite, and clinoptilolite. The preferred crystalline aluminosilicates are ZSM-5, ZSM-11, ZSM-12, ZSM-21, and TEA mordenite, with ZSM-5 particularly preferred.

The preferred acidic crystalline aluminosilicates components are those having a crystal density, in the dry hydrogen form, of not substantially below about 1.6 grams per cubic centimeter. It has been found that zeolites which satisfy all three of these criteria are most desired because they tend to maximize the production of gasoline boiling range hydrocarbon products and valuable aromatic hydrocarbons such as benzene, toluene and xylenes. Therefore, the preferred zeolites are those having a constrainst index as defined above of about 1 to 12, a silica-to-alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 11 of the article on Zeolite Structure by W. M. Meier. This paper, the entire contents of which are incorporated herein by reference, is included in "Proceedings of the Conference on Molecular Sieves," London, April 1967, published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

The zeolite to be used for the crystalline aluminosilicate component in this invention in all cases should be acidic as evidenced by some degree of catalytic activity for cracking of normal hexane. When, in the process of this invention, it is desired to maximize the yield of aromatic hydrocarbons, the degree of acidity as evidenced in a hexane-cracking test which gives an alpha value of at least 10 is required. The alpha value is to be determined in accordance with the method set forth by P. B. Weisz and J. N. Miale in "Journal of Catalysis", Vol. 4, No. 4, August 1969, pp. 527–529, which description is herein incorporated by reference. The alpha value is determined before this component is formed into an intimate mixture with the carbon monoxide reducing component.

The heterogeneous catalysts may be prepared in various ways. The two components may be separately prepared in the form of catalyst particles such as pellets or extrudates, for example, and simply mixed in the required proportions. The particle size of the individual component particles may be quite small, for example, from about 20 to about 150 microns, when intended for use in fluid bed operation; or they may be as large as up to about ½ inch for fixed bed operation. Or, the two components may be mixed as powders and formed into pellets or extrudate, each pellet containing both components in substantially the required proportions. Binders such as clays may be added to the mixture. Alternatively, the component that has catalytic activity for the reduction of carbon monoxide may be formed on the acidic crystalline aluminosilicate component by conventional means such as impregnation of that solid with salt solutions of the desired metals, followed by drying and calcination. Base exchange of the acidic crystalline aluminosilicate component also may be used in some selected cases to effect the introduction of part or all of the carbon monoxide reduction component. Other means for forming the intimate mixture may be used, such as: precipitation of the carbon monoxide reduction component in the presence of the acidic crystalline aluminosilicate; or electroless deposition of metal on the zeolite; or deposition of metal from the vapor phase. Various combinations of the above preparative methods will be obvious to those skilled in the art of catalyst preparation. It should be cautioned, however, to avoid techniques likely to reduce the crystallinity of the acidic crystalline aluminosilicate.

It will be recognized from the foregoing description that the heterogeneous catalysts, i.e., the above-described intimate mixtures, used in the process of this invention, may have varying degrees of intimacy. At one extreme, when using ½ inch pellets of the carbon monoxide reducing component mixed with ½ inch pellets of the acidic crystalline aluminosilicate, substantially all locations within at least one of the components will be within not more than about ½ inch of some of the other component, regardless of the proportions in which the two components are used. With different sized pellets, e.g., ½ inch and ¼ inch, again substantially all locations within at least one of the components will be within not more than about ½ inch of the other component. These examples illustrate the lower end of the degree of intimacy required for the practice of this invention. At the other extreme, one may ball mill together acid crystalline aluminosilicate particles of about 0.1 micron particle size with colloidal iron oxide of similar particle size followed by pelletization. For this case, substantially all the locations within at least one of the components will be within not more than about 0.1 micron of some of the other component. This exemplifies about the highest degree of intimacy that is practical. The degree of intimacy of the physical mixture may also be expressed as the minimum distance of separation of the central points located within the particles of the two components. This will, on average, be represented by one-half the sum of the average particle size for the two components. Thus, for the foregoing example illustrating the highest degree of intimacy, the centers of the particles of either of the two components will be separated from the nearest particle of the other component by an average distance of at least about 0.1 micron. The degree of intimacy of the heterogeneous catalyst is largely determined by its method of preparation, but it may be independently verified by physical methods such as visual observations, examination in an ordinary microscope or with an electron microscope, or by electron microprobe analysis.

In the process of this invention, synthesis gas is contacted with the heterogeneous catalyst at a temperature of from about 400° F to 1000° F, preferably from 500° F to 850° F, at a pressure from 1 to 1000 atmospheres, preferably from 3 to 200 atmospheres, and at a volume hourly space velocity from about 500 to 50,000 volumes of gas, at standard temperature and pressure per volume of catalyst, or equivalent contact time if a fluidized bed is used. The heterogeneous catalyst may be contained as a fixed bed, or a fluidized bed may be used. The product stream containing hydrocarbons, unreacted gases and steam may be cooled and the hydrocarbons recovered by any of the techniques known in the art, which techniques do not constitute part of this invention. The recovered hydrocarbons may be further separated by distillation or other means to recover one or more products such as high octane gasoline, propane fuel, benzene, toluene, xylenes, or other aromatic hydrocarbons.

EXAMPLES

Example 1

Thoria was prepared according to the method of Pichler and Ziesecke, as described in "The Isosynthesis,"U.S. Burea of Mines Bulletin, 488 (1950), which involved essentially the precipitation of $Th(NO_3)_4$ solutions with $Na_2CO_3$ solutions followed by filtration, washing and drying at 100° C.

A composite catalyst was prepared by ball-milling equal weights of $NH_4ZSM$-5 and dried thoria gel, pelleting and calcining at 1000° F for 10 hours. Three experiments were done, each one at 800° F, 1215 psia, and with a mixture of hydrogen and carbon monoxide having a $H_2/CO$ ratio of 1.0. The first and second runs involved the thorium oxide and HZSM-5, each used separately, while the third run employed a heterogeneous catalyst containing both thorium oxide and HZSM-5.

The results are summarized in Table 1.

TABLE 1

| Catalyst | (A) $ThO_2$ Alone | (B) HZSM-5 Alone | (C) $ThO_2$ plus HZSM-5 Composite |
|---|---|---|---|
| Contact Time - seconds (at reaction conditions) | 15 | 15 | 15 |
| Conversion, wt. % | | | |
| CO | 5.3 | <1 | 22.4 |
| $H_2$ | 2.6 | <1 | 15.2 |
| Wt. % Hydrocarbons in total reaction effluent | 0.6 | 0.2 | 5.5 |
| Hydrocarbon Distribution (wt. %) | | | |
| Methane | 41.0 | 39.6 | 17.3 |
| $C_2$-$C_4$ hydrocarbons | 58.6 | 60.4 | 73.8 |
| $C_5^+$ | 0.4 | — | 8.9 |
| | 100.0 | 100.0 | 100.0 |
| Aromatics in $C_5^+$, wt. % | Trace | Trace | 41.6 |

Example 2

A ZnO supported on $Al_2O_3$ was obtained from a commercial source and was used as the carbon monoxide reducing component. It contained 24% by weight of ZnO. HZSM-5 was used as the acidic crystalline aluminosilicate component.

The heterogeneous composite catalyst was prepared by ball-milling together four parts of the HZSM-5 to one part of the $ZnO/Al_2O_3$ catalyst, followed by pelletizing. Two runs were carried out, both at 600° F, 750 psia, and with a mixture of hydrogen and carbon monoxide having a $H_2/CO$ ratio of 4. The first run used the $ZnO/Al_2O_3$ catalyst alone, while the second run employed a composite catalyst containing both the $ZnO/Al_2O_3$ and HZSM-5 catalysts.

The results are shown in Table 2.

TABLE 2

| Catalyst | (D) $ZnO/Al_2O_3$ Alone | (E) 20% $ZnO/Al_2O_3$ plus 80% HZSM-5 Composite |
|---|---|---|
| Contact Time - seconds (at reaction conditions) | 25 | 25 |
| Conversion, wt. % | | |
| CO | 32.0 | 6.7 |
| $H_2$ | 5.4 | 3.4 |
| Wt. % hydrocarbons in total reaction effluent | 0.2 | 1.0 |
| Hydrocarbon Distribution (wt. %) | | |
| Methane | 100.0 | 11.4 |
| $C_2$-$C_4$ hydrocarbons | — | 42.9 |
| $C_5^+$ | — | 45.7 |

TABLE 2-continued

| Catalyst | (D) ZnO/Al$_2$O$_3$ Alone | (E) 20% ZnO/Al$_2$O$_3$ plus 80% HZSM-5 Composite |
|---|---|---|
| | 100.0 | 100.0 |
| Aromatics in C$_5$+ (wt. %) | None | 71.8 |

Example 3

A methanol synthesis catalyst was prepared containing the following percentages by weight; copper — 54.55, zinc — 27.27, chromium — 9.09, and lanthanum — 9.09 on an oxygen-free basis. A composite catalyst was then prepared from equal parts of this component and HZSM-5, using 5% graphite as a binder. Two runs were made, each at 600° F, 750 psia, using as a feed a mixture of hydrogen and carbon monoxide with a H$_2$/CO ratio of 2 and are summarized in Table 3.

Table 3

| Catalyst | (F) Methanol Type Alone | (G) Methanol Type plus HZSM-5 Composite |
|---|---|---|
| Space Velocity on Methanol Catalyst Component (cc of synthesis gas/g. of methanol catalyst/hour) | 5825 | 6764 |
| CO Conversion wt. % | 24 | 34 |
| Wt. % in Water-Free Product | | |
| Methane | 0.7 | 1.1 |
| C$_2$-C$_4$ Hydrocarbons | 1.0 | 5.7 |
| C$_5$+ Hydrocarbons | 1.0 | 1.8 |
| | 2.7 | 8.6 |

As shown, the contact times (reciprocal of space velocity) relative to the methanol catalyst component are very similar in the two runs; being slightly lower with the composite catalyst.

The composite catalyst shows a much greater production of hydrocarbons, particularly hydrocarbons higher in carbon number than methane, than the carbon monoxide reducing component by itself.

Example 4

The carbon monoxide reducing component was a commercial ion oxide type ammonia synthesis catalyst containing small amounts of K, Ca and Al promoters. The zeolite component contained 65% HZSM-5 and 35% alumina binder. The heterogeneous composite catalyst contained 75% of the iron component and 25% of the zeolite component, and was made by ball-milling the components and then pelleting the resultant powder.

Three runs were made at 700° C, 265 psia and with a mixture of hydrogen and carbon monoxide having a H$_2$/CO ratio of 1.0. Results are summarized in Table 4.

TABLE 4

| Catalyst | (H) Fe Component Alone | (J) Fe/HZSM-5 Components not mixed. Components in separate reaction zones in series | (K) Fe+HZSM-5 Composite catalyst single reaction zone |
|---|---|---|---|
| Contact time, - seconds (at reaction conditions) | 15 | 30 | 15 |
| Conversion, wt. % | | | |
| CO | 93.5 | 96.9 | 98.4 |
| H$_2$ | 67.8 | 76.9 | 72.3 |
| Wt. % Hydrocarbons in total reaction effluent | 22.6 | 25.6 | 25.5 |
| Hydrocarbon Distribution (wt. %) | | | |
| Methane | 44.6 | 50.1 | 52.6 |
| C$_2$-C$_4$ hydrocarbons | 50.1 | 41.1 | 41.4 |
| C$_5$+ | 5.3 | 8.8 | 6.0 |
| Aromatics in C$_5$+, wt. % | 1.9 | 2.3 | 15.0 |

Experiment H illustrates the selectivity of the iron component in the absence of HZSM-5; the C$_5$+ hydrocarbons contain only 1.9% aromatics. In experiment, (j), a reaction zone containing HZSM-5 was placed after the reaction zone containing the iron catalyst. It can be seen that the aromatics selectivity was not significantly changed. In experiment (k), however, the intimate mixture of HZSM-5 with the iron component gave about a seven-fold increase in aromatics selectivity.

Example 5

The catalyst in this example was prepared by impregnation of NH$_4$ZSM-5 containing 35% alumina binder with a solution of Fe(NO$_3$)$_3$, drying the catalyst and calcining at 1000° F for 10 hours. The finished catalyst contained 3% iron. Synthesis gas (H$_2$/CO = 1) was reacted over this catalyst at 700° F, 515 psia and 30 seconds contact time, giving the following conversions and products.

TABLE 5

| Catalyst | FeHZSM-5 |
|---|---|
| Contact Time - seconds (at reaction conditions) | 30 |
| Conversion, wt. % | |
| CO | 19.7 |
| H$_2$ | 12.0 |
| Wt. % Hydrocarbons in total reaction effluent | 8.1 |
| Hydrocarbon Distribution (wt. %) | |
| Methane | 33.4 |
| C$_2$-C$_4$ hydrocarbons | 47.5 |
| C$_5$+ | 19.1 |
| Aromatics in C$_5$+, wt. % | 24.6 |

Example 6

The catalyst in this example was an intimate mixture of 57.4% ilmenite sand (FeO.TiO$_2$), 21.3% HZSM-5 and 21.3% alumina binder. Synthesis gas (H$_2$/CO = 1) was reacted over said catalyst at 700° F, and 265 psia and 10 seconds contact time, giving the following conversion and products.

TABLE 6

| Catalyst | Ilmenite + HZSM-5 |
|---|---|
| Contact Time - seconds | 10 |

TABLE 6-continued

| Catalyst | Ilmenite + HZSM-5 |
|---|---|
| (at reaction conditions) | |
| Conversion, wt. % | |
| CO | 62.3 |
| $H_2$ | 48.3 |
| Wt. % Hydrocarbons in | |
| total reaction effluent | 21.5 |
| Hydrocarbon Distribution (wt. %) | |
| Methane | 29.2 |
| $C_2$-$C_4$ hydrocarbons | 59.1 |
| $C_5^+$ | 11.7 |
| Aromatics in $C_5^+$, wt. % | 29.9 |

Example 7

The catalyst in this example was an intimate mixture of 41.2% magnetite ($Fe_3O_4$), 29.4% HZSM-5 and 29.4% alumina binder. Synthesis gas ($H_2$/CO = 1) was reacted over said catalyst at 700° F, 265 psia and 10 seconds contact time, giving the following conversions and products.

TABLE 7

| Catalyst | Magnetite + HZSM-5 |
|---|---|
| Contact Time - seconds | 10 |
| (at reaction conditions) | |
| Conversion, wt. % | |
| CO | 41.8 |
| $H_2$ | 37.6 |
| Wt. % Hydrocarbons in | |
| total reaction effluent | 16.6 |
| Hydrocarbon Distribution (wt. %) | |
| Methane | 31.0 |
| $C_2$-$C_4$ hydrocarbons | 55.0 |
| $C_5^+$ | 14.0 |
| Aromatics in $C_5^+$, wt. % | 19.9 |

Example 8

The catalyst in this example was an intimate mixture of 41.2% iron carbide, 29.4% HZSM-5 and 29.4% alumina binder. Synthesis gas ($H_2$/CO = 1) was reacted over said catalyst at 700° F, 265 psia and 10 seconds contact time, giving the following conversions and products.

TABLE 8

| Catalyst | Iron carbide + HZSM-5 |
|---|---|
| Contact Time - seconds | 10 |
| (at reaction conditions) | |
| Conversion, wt. % | |
| CO | 11.7 |
| $H_2$ | 11.1 |
| Wt. % Hydrocarbons in | |
| total reaction effluent | 4.5 |
| Hydrocarbon Distribution (wt. %) | |
| Methane | 40.8 |
| $C_2$-$C_4$ hydrocarbons | 50.1 |
| $C_5^+$ | 9.1 |
| Aromatics in $C_5^+$, wt. % | 6.2 |

Example 9

The catalyst in this example was an intimate mixture of 50% thoria and 50% rare-earth-exchanged zeolite Y (faujasite). Synthesis gas ($H_2$/CO = 1) was reacted over said catalyst at 800° F, 1215 psia and 15 seconds contact time, giving the following conversion and products.

TABLE 9

| Catalyst | $ThO_2$ + REY |
|---|---|
| Contact Time - seconds | 15 |
| (at reaction conditions) | |
| Conversion, wt. % | |
| CO | 5.3 |
| $H_2$ | 2.9 |
| Wt. % Hydrocarbons in | |

TABLE 9-continued

| Catalyst | $ThO_2$ + REY |
|---|---|
| total reaction effluent | 0.8 |
| Hydrocarbon Distribution (wt. %) | |
| Methane | 42.8 |
| $C_2$-$C_4$ hydrocarbons | 54.7 |
| $C_5^+$ | 2.5 |
| Aromatics in $C_5^+$, wt. % | 68.0 |

It has further been discovered that synthesis gas containing sulfur moieties, such as hydrogen sulfide, may be efficiently converted to hydrocarbons by contacting such synthesis gas with a special catalyst composition, with the above composition, which is relatively insensitive to sulfur and whose activity and selectivity may even be improved as well as restored after continuous exposure to sulfur moieties in the synthesis gas feed. This aspect of this invention is concerned with the catalytic conversion of such sulfur containing synthesis gas to desired hydrocarbon products including gasoline boiling range aromatics and/or olefins wherein the catalyst is continuously or intermittently subjected either by design or by accident to contact with sulfur components in the synthesis gas.

The special catalyst used in this aspect of this invention is a crystalline aluminosilicate zeolite having physical properties as described above, such as ZSM-5, in admixture with a carbon monoxide reducing component comprising thorium as a metal, oxide and/or sulfide thereof which may or may not additionally have molybdenum in admixture therewith.

Example 10

The addition of ZSM-5 crystalline zeolite to a $ThO_2$ catalyst has enhanced activity, shifts the formed aromatics from $C_{11}+$ aromatics to primarily $C_{10}-$ aromatics and dramatically inhibits methane formation. It has also been observed that the addition of $Al_2O_3$ to a $ThO_2$/ZSM-5 catalyst combination improves the selectivity of the catalyst to form aromatics.

The data presented in Table 11 below demonstrate the effect of adding ZSM-5 crystalline zeolite on the activity and selectivity of a $ThO_2$ isosynthesis catalyst. Typical isosynthesis process conditions and yields are shown in Example 10 of Table 11. The process is normally operated at 4400 psig and yields isobutane as a major product. Some aromatics (mainly $C_{11}+$) are made as well as oxygenates. The high pressure of the operation is considered necessary to overcome a thermodynamic limitation on one the primary steps in the reaction and not because of a kinetic limitation. The effect of reducing the pressure to 1200 psig is shown in Examples 2A and 2B of Table 11. It will be noted that a decrease in conversion is obtained. However, the most striking effect is the change in selectivity. Methane becomes the predominate product while isobutane yield is greatly reduced. In addition, it is observed that more olefins are formed. From Example 12, it is seen that changing the $ThO_2$/$Al_2O_3$ ratio from 5 to 4 has little effect on activity or selectivity. The liquid hydrocarbons produced in Examples 11 and 12 are mainly $C_{10}+$ hydrocarbons.

The effect of adding ZSM-5 to the catalyst of Example 12 is shown in Examples 13A and B of Table 11. The WHSV's were based on $ThO_2$/$Al_2O_3$, the component with highest density. Equivalent VHSV's were achieved by maintaining comparable reactor volumes in an effort to keep gas residence times at approximately equal levels. From these examples an enhancement in activity is observed with ZSM-5 addition as well as a dramatic change in selectivity.

In the presence of ZSM-5, methane levels are greatly reduced while LPG components increase. The predominate products are aromatics and they are largely trimethyl-benzenes as shown in Table 12 below. In Example 13 it is further observed that conversion levels drop (261 hours on stream) but aromatic yields are significantly higher.

Example 11

Table 13 below presents the data obtained on various $ThO_2$ (no alumina) catalysts. The activity of a pure $ThO_2$ catalyst at 1200 psig, 800° F and 2.2 WHSV is shown in Example 14 of the table. The effect of added ZSM-5 is seen in Examples 15A and B. The main effects to be observed are enhanced conversion and reduced methane make. However, the selectivity to aromatics is lower than that observed with the $Al_2O_3$ containing

TABLE 11

EFFECT OF ZSM-5 ON $ThO_2/Al_2O_3$ IN SYNGAS CONVERSION ($H_2/CO = 1$)

| Example Run Ident. | 10 Isosynthesis | 11A LPA 117B | 11B LPA 117C | 12 LPA 118A | 13A LPA 97E | 13B LPA 97G |
|---|---|---|---|---|---|---|
| Catalyst Composition, wt% | | | | | | |
| $ThO_2$ | 83 | 83 | 83 | 80 | 40 | 40 |
| $Al_2O_3$ | 17 | 17 | 17 | 20 | 10 | 10 |
| ZSM-5 | 0 | 0 | 0 | 0 | 50 | 50 |
| Reaction Conditions | | | | | | |
| Temperature, °F | 797 | 800 | 800 | 800 | 800 | 800 |
| Pressure, psig | 4400 | 1200 | 1200 | 1200 | 1200 | 1200 |
| WHSV, $hr^{-1}$ (a) | 0.33 | 0.38 | 1.4 | 1.3 | 1.4 | 1.4 |
| VHSV, $hr^{-1}$ | 600 | 240 | 900 | 840 | 900 | 900 |
| Time on stream, hr | 72 | 46 | 69 | 61 | 165 | 261 |
| Conversion, wt% | | | | | | |
| CO | 73 | 18.2 | 11.8 | 11.2 | 21.2 | 18.0 |
| $H_2$ | 67 | 17.2 | 14.2 | 8.9 | 36.4 | 18.9 |
| Effluent Composition, wt% | | | | | | |
| Hydrocarbons | | 3.4 | 2.3 | 2.6 | 5.8 | 5.9 |
| Oxygenates | | 0.6 | 0.7 | 0.5 | — | — |
| $H_2O$ | | 0.6 | 0.1 | 0.8 | 1.6 | 1.4 |
| $CO_2$ | | 13.7 | 8.9 | 7.1 | 14.8 | 10.8 |
| CO | | 76.3 | 82.3 | 82.9 | 73.5 | 76.5 |
| $H_2$ | | 5.5 | 5.7 | 6.1 | 4.3 | 5.4 |
| Hydrocarbons, wt% | | | | | | |
| Methane | 15.0 | 47.1 | 41.0 | 47.5 | 1.8 | 5.2 |
| Ethane | 4.8 | 6.6 | 4.4 | 5.4 | 18.9 | 15.6 |
| Ethylene | — | 4.0 | 3.3 | 3.0 | 0.3 | 0.3 |
| Propane | 4.3 | 4.1 | 2.6 | 2.2 | 20.1 | 13.8 |
| Propylene | — | 4.8 | 3.9 | 3.1 | 0.3 | 0.2 |
| i-Butane | 46.6 | 2.7 | 1.7 | 1.0 | 3.7 | 2.0 |
| n-Butane | 5.2 | 0.2 | 0.1 | — | 2.2 | 0.2 |
| Butenes | 6.0 | 6.1 | 7.1 | 3.0 | — | — |
| $C_5^+$ PON | 11.7 | 9.6 | 26.9 | 24.9 | 3.8 | 2.2 |
| Aromatics | 7.4(b) | 14.8 | 9.0 | 13.0(d) | 48.9(d) | 60.7 |
| Total $C_5^+$ | 19.1 | 24.4(c) | 35.9(c) | 37.9(c) | 52.7 | 62.9 |
| Aromatics in $C_5^+$ | 38.7 | 60.7 | 25.1 | 34.3 | 92.8 | 96.5 |

(a) WHSV based on $ThO_2/Al_2O_3$ component
(b) 79% $C_{11}^+$
(c) 44–45% $C_{10}^+$
(d) cf. Table 3 for aromatic distribution

TABLE 12

AROMATICS DISTRIBUTION

| Run Ident. | LPA 118A | LPA 97E | LPA 97G |
|---|---|---|---|
| Catalyst Composition, wt% | | | |
| $ThO_2$ | 80 | 40 | 40 |
| $Al_2O_3$ | 20 | 10 | 10 |
| ZSM-5 | 0 | 50 | 50 |
| Aromatics in HC, wt% | 13.0 | 48.9 | 60.7 |
| Aromatics Distribution, wt% | | | |
| Benzene | — | 0.1 | — |
| Toluene | — | 1.7 | 1.3 |
| Ethylbenzene | 3.3 | 0.1 | 0.1 |
| Xylenes | 14.5 | 29.5 | 18.2 |
| Trimethylbenzenes | 29.9 | 56.6 | 62.9 |
| Other $A_9$ | 12.5 | 0.6 | 0.4 |
| $A_{10}$ | 28.4 | 21.0 | 17.1 |
| $A_{11}^+$ | 11.4 | — | — |
| | 100.0 | 100.0 | 100.0 | catalysts.

Combinations of $ThO_2$ with other zeolites, dealuminized erionite and REY crystalline zeolite, were listed for syngas conversion and reported in Examples 16 and 17 of Table 13. The erionite containing catalyst appears to also enhance conversion and depress methane formation. The hydrocarbons formed, however, are mainly low molecular weight hydrocarbons and non-aromatic. However, relatively high selectivity to ethylene and propylene is observed with the erionite containing catalyst. The REY component appears to contribute little more than a diluent when comparing Examples 14 and 17.

The inhibition of methane formation in the examples comprising a ZSM-5 crystalline zeolite and an erionite type of crystalline zeolite is a clear indication that an intermediate species in the reaction sequence is being intercepted since methane, once formed, is quite stable under the operating conditions employed.

TABLE 13

ACTIVITY OF VARIOUS $ThO_2$ CATALYSTS FOR SYNGAS CONVERSION ($H_2/CO = 1$)

| Example Run Ident. | 14 LPA 78A | 15A LPA 79C | 15B LPA 79E | 16 LPA 90A | 17 LPA 80A |
|---|---|---|---|---|---|
| Catalyst Composition, wt% | | | | | |
| $ThO_2$ | 100 | 50 | 50 | 50 | 50 |

TABLE 13-continued

| ACTIVITY OF VARIOUS ThO$_2$ CATALYSTS FOR SYNGAS CONVERSION (H$_2$/CO = 1) | | | | | |
|---|---|---|---|---|---|
| Example | 14 | 15A | 15B | 16 | 17 |
| Run Ident. | LPA 78A | LPA 79C | LPA 79E | LPA 90A | LPA 80A |
| ZSM-5 | 0 | 50 | 50 | 0 | 0 |
| Other zeolite | 0 | 0 | 0 | 50 Erionite[b] | 50 REY |
| Reaction Conditions | | | | | |
| Temperature, °F | 800 | 800 | 800 | 800 | 800 |
| Pressure, psig | 1200 | 1200 | 1200 | 1200 | 1200 |
| WHSV, hr$^{-1}$ [a] | 2.2 | 3.4 | 0.36 | 3.7 | 2.5 |
| Time on Stream, hr | 92 | 171 | 267 | 5 | 19 |
| Conversion, % | | | | | |
| CO | 5.3 | 11.8 | 57.2 | 11.3 | 5.3 |
| H$_2$ | 2.6 | 17.4 | 47.8 | 12.6 | 2.9 |
| Hydrocarbons, wt% | | | | | |
| Methane | 41.0 | 17.3 | 11.3 | 13.7 | 42.8 |
| Ethane | 5.5 | 27.6 | 28.0 | 22.6 | 15.6 |
| Ethylene | 1.7 | 0.6 | 0.1 | 27.0 | 1.5 |
| Propane | 7.8 | 25.6 | 24.8 | 7.6 | 7.3 |
| Propylene | 3.1 | 1.3 | 0.2 | 13.3 | 3.6 |
| i-Butane | — | 12.1 | 4.3 | 3.7 | 3.1 |
| n-Butane | — | 6.6 | 2.7 | 1.1 | 0.2 |
| Butenes | 36.9 | — | — | 9.6 | 23.4 |
| C$_5$+PON | 0.4 | 5.2 | 0.9 | 1.4 | 0.8 |
| Aromatics | — | 3.7 | 27.7 | — | 1.7 |
| Total C$_5$+ | 0.4 | 8.9 | 28.6 | 1.4 | 2.5 |

[a]WHSV based on ThO$_2$ component
[b]Dealuminized, SiO$_2$/Al$_2$O$_3$ = 16.3

Synthesis gas containing ~ 2% H$_2$S has been converted to aromatic hydrocarbons over ThO$_2$/Al$_2$O$_3$/HZSM-5. The catalyst was found to be resistant to sulfur poisoning. This is demonstrated in the attached Table 14.

The catalyst was a sample of spent catalyst from Run LPA 97 which had previously accumulated 261 hours on stream. Despite the fact that the spent catalyst had, in the interim, been exposed to air, the sample was found to be active after a simple pre-treatment with H$_2$ (LPA 125 A).

Sulfur (2% H$_2$S) was added to the syngas feed (LPA 125 B). The lowered space velocity was a result of experimental difficulties. However, the results clearly demonstrate the ability of the catalyst to function in the presence of sulfur. The effect of sulfur is mainly to increase methane. In LPA 125 C, the S was removed, methane decreased while aromatics increased. Sulfur was re-admitted (LPA 125 D) at a higher (than LPA 125 B) WHSV, upon which methane again increased. Finally (LPA 125 E) upon removal of S, methane decreased and aromatics increased.

Comparison of LPA 125 A and E indicates an induction period for aromatics formation. This behavior has been previously observed in ThO$_2$/HZSM-5 (no Al$_2$O$_3$). Zirconia catalysts, on the other hand, exhibit no such induction period.

Table 14

| EFFECT OF H$_2$S ON ThO$_2$/Al$_2$O$_3$/HZSM-5[c] SYNGAS CONVERSION ACTIVITY | | | | | |
|---|---|---|---|---|---|
| | (H$_2$/CO = 1) | | | | |
| Run LPA 125 - | A | B<br>+ 2% H$_2$S | C | D<br>+ 2% H$_2$S | E |
| Reaction Conditions | | | | | |
| Temperature, °F | ← | | 800 | | → |
| Pressure, psig | ← | | 1200 | | → |
| WHSV hr$^{-1}$ [a] | 1.1 | 0.42 | 1.4 | 0.9 | 0.9 |
| Time on stream hr | 21 | 27½ | 93½ | 113 | 136½ |
| Conversion, % | | | | | |
| CO | 16.6 | 19.9 | 15.4 | 17.8 | 16.7 |
| H$_2$ | 15.8 | 15.4 | 13.9 | 17.8 | 13.5 |
| Total Effluent, wt% | | | | | |
| Hydrocarbons | 3.7 | 7.0 | 4.5 | 6.1 | 6.2 |
| H$_2$O | 0.8 | 2.3 | 1.2 | 1.5 | 0.6 |
| CO$_2$ | 12.0 | 10.3 | 9.6 | 10.1 | 9.7 |
| CO | 77.8 | 74.7 | 79.0 | 76.7 | 77.8 |
| H$_2$ | 5.6 | 5.7 | 5.7 | 5.5 | 5.8 |

Table 14-continued

| EFFECT OF H$_2$S ON ThO$_2$/Al$_2$O$_3$/HZSM-5[c] SYNGAS CONVERSION ACTIVITY | | | | | |
|---|---|---|---|---|---|
| | (H$_2$/CO = 1) | | | | |
| other[b] | 0.1 | TR | — | TR | — |
| Hydrocarbons, wt% | A | B | C | D | E |
| Methane | 5.6 | 16.9 | 5.3 | 23.1 | 8.4 |
| Ethane | 21.3 | 17.3 | 11.8 | 9.2 | 12.1 |
| Ethylene | 0.2 | 0.2 | 0.4 | 0.6 | 0.2 |
| Propane | 24.4 | 12.1 | 11.0 | 9.6 | 7.6 |
| Propylene | 0.4 | — | 0.4 | 0.2 | 0.3 |
| i-Butane | 7.5 | 2.3 | 3.5 | 4.2 | 3.0 |
| n-Butane | 4.1 | 0.5 | 1.8 | 1.3 | 1.6 |
| Butenes | — | — | — | — | — |
| C$_5$+ PON | 1.9 | 0.1 | 1.7 | 1.1 | 1.4 |
| Aromatics | 34.6 | 50.6 | 64.2 | 50.8 | 65.5 |

[a]Based on ThO$_2$/Al$_2$O$_3$ component
[b]Oxygenates or COS
[c]40/10/50 parts by weight

What is claimed is:

1. A method for producing hydrocarbons, which comprises: contacting synthesis gas having a ratio of hydrogen-to-carbon oxides of from 0.2 to 6.0 with a heterogeneous catalyst at a temperature of from 500° F to 850° F and at a pressure of from 1 atmosphere to 1000 atmospheres, and at a volume hourly space velocity from 500 to 50,000 volumes of gas at standard temperature and pressure per volume of said heterogeneous catalyst said heterogeneous catalyst comprising an intimate mixture of an inorganic carbon monoxide reducing catalyst and a selective acidic crystalline aluminosilicate that has pore diameter greater than about 5 Angstroms; a silica-to-alumina ratio of at least 12; a constraint index within the range of 1 to 12; and, recovering hydrocarbons containing quantities of aromatic hydrocarbons.

2. The method of claim 1 wherein said inorganic substance characterized by catalytic activity for the reduction of carbon monoxide constitutes from about one weight percent to about eighty weight percent of the active components of said heterogeneous catalyst.

3. The method of claim 1 wherein said inorganic substance and said acidic crystalline aluminosilicate are in the same catalyst particle.

4. The method of claim 1 wherein said inorganic substance and said acidic crystalline aluminosilicate are in separate catalyst particles.

5. The method described in claim 1, wherein said acidic crystalline aluminosilicate is a H-ZSM-5 crystalline zeolite.

6. The method described in claim 5, wherein said carbon monoxide reducing catalyst is a Fischer-Tropsch catalyst and wherein aromatic hydrocarbons are separated from said recovered hydrocarbons.

7. The method described in claim 1, wherein said acidic crystalline aluminosilicate is H-ZSM-11 crystalline zeolite.

8. The method described in claim 1, wherein said inorganic substance comprises iron.

9. The method of claim 1, wherein the increased quantity of aromatic hydrocarbons are rich in toluenes and xylenes.

10. The method claimed in claim 1 wherein said catalyst is formulated from a metal or compound of zinc, iron, cobalt, nickel, ruthenium, thorium, rhodium, osmium or mixtures thereof.

* * * * *

UNITED STATES PATENT AND TRADEMARK OFFICE
CERTIFICATE OF CORRECTION

PATENT NO. : 4,086,262
DATED : April 25, 1978
INVENTOR(S) : CLARENCE D. CHANG, WILLIAM H. LANG and ANTHONY J. SILVESTRI It is certified that error appears in the above-identified patent and that said Letters Patent are hereby corrected as shown below:

| | |
|---|---|
| Column 4, line 66 | "350°" should be --360°--. |
| Column 5, line 3 | After "compounds" add --,--. |
| Column 6, line 23 | "alumina" should be --aluminum--. |
| Column 12, line 3 | "700°C" should be --700°F--. |
| Column 12, line 28 | After "experiment" delete --,--. |
| Column 14, line 50 | After "one" insert --of--. |
| Column 17, line 61 (Table 14) | "WHSV $hr^{-1(a)}$" should be --WHSV $hr^{-1(a)}$--. |
| Column 18, line 53 (Claim 1) | After "has" insert --a--. |

Signed and Sealed this

Third Day of October 1978

[SEAL]

Attest:

RUTH C. MASON
Attesting Officer

DONALD W. BANNER
Commissioner of Patents and Trademarks